United States Patent [19]

Grundei

[11] Patent Number: 4,898,161
[45] Date of Patent: Feb. 6, 1990

[54] FORCEPS FOR PUSHING APART VERTEBRAE

[75] Inventor: Hans Grundei, Lübeck, Fed. Rep. of Germany

[73] Assignee: S+G Implants GmbH, Lubeck, Fed. Rep. of Germany

[21] Appl. No.: 124,917

[22] Filed: Nov. 24, 1987

[30] Foreign Application Priority Data

Dec. 12, 1986 [DE] Fed. Rep. of Germany ....... 3641279
Mar. 3, 1987 [DE] Fed. Rep. of Germany ....... 3707097

[51] Int. Cl.⁴ ............................ A61F 5/04; B25B 7/12; B25B 7/04
[52] U.S. Cl. ..................................... 606/105; 81/342; 81/356
[58] Field of Search .......... 128/92 VZ, 92 V, 92 VY, 128/92 VT, 69, 92 EC, 92 EB, 321, 322, 323, 324, 346, 348.1, 352, 354; 81/355, 361, 362, 386, 405, 342, 356

[56] References Cited

U.S. PATENT DOCUMENTS

| | | | |
|---|---|---|---|
| 1,315,235 | 9/1919 | Olsen | 81/355 |
| 1,985,108 | 12/1934 | Rush | 128/92 VZ |
| 2,427,128 | 9/1947 | Ettinger | 128/92 VZ |
| 3,509,882 | 5/1970 | Blake | 128/346 |
| 3,510,923 | 5/1970 | Blake | 128/346 |
| 4,445,513 | 5/1984 | Ulrich et al. | 128/69 |
| 4,567,884 | 2/1986 | Edwards | 128/69 |
| 4,706,660 | 11/1987 | Petersen | 128/92 VZ |

FOREIGN PATENT DOCUMENTS 1132930 6/1982 U.S.S.R. ........................ 128/92 V

Primary Examiner—Mickey Yu
Assistant Examiner—Michael Brown
Attorney, Agent, or Firm—Balogh, Osann, Kramer, Dvorak, Genova & Traub

[57] ABSTRACT

Forceps for pushing apart adjacent vertebrae that has two parallel pins connected or connectible to a pair of jaws, one pin being displaceable towards and away from the other pin by the moving of a guide when the jaws are being spread apart, the guide ensuring that the pins remain parallel to one another during such movement.

2 Claims, 2 Drawing Sheets

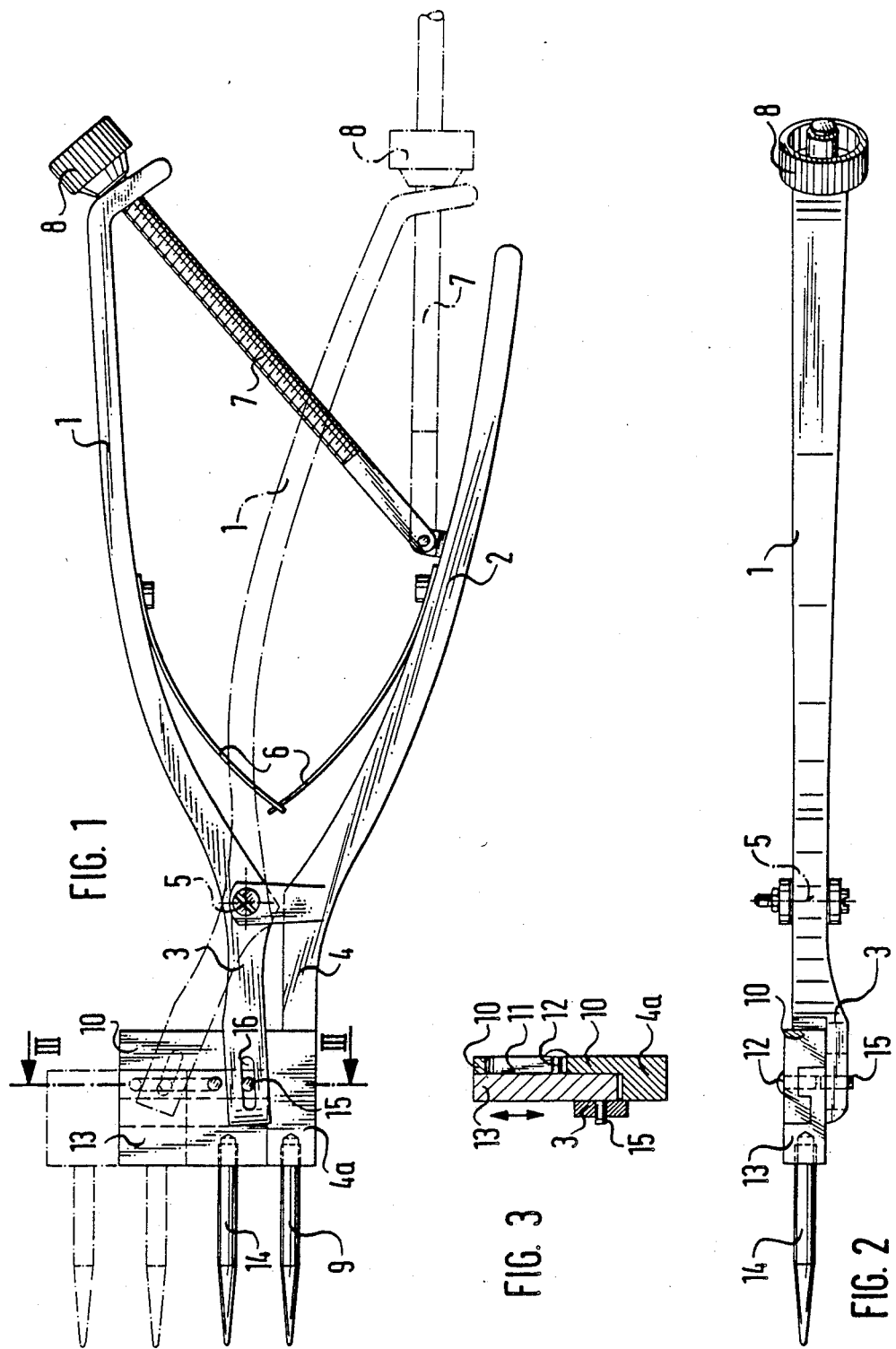

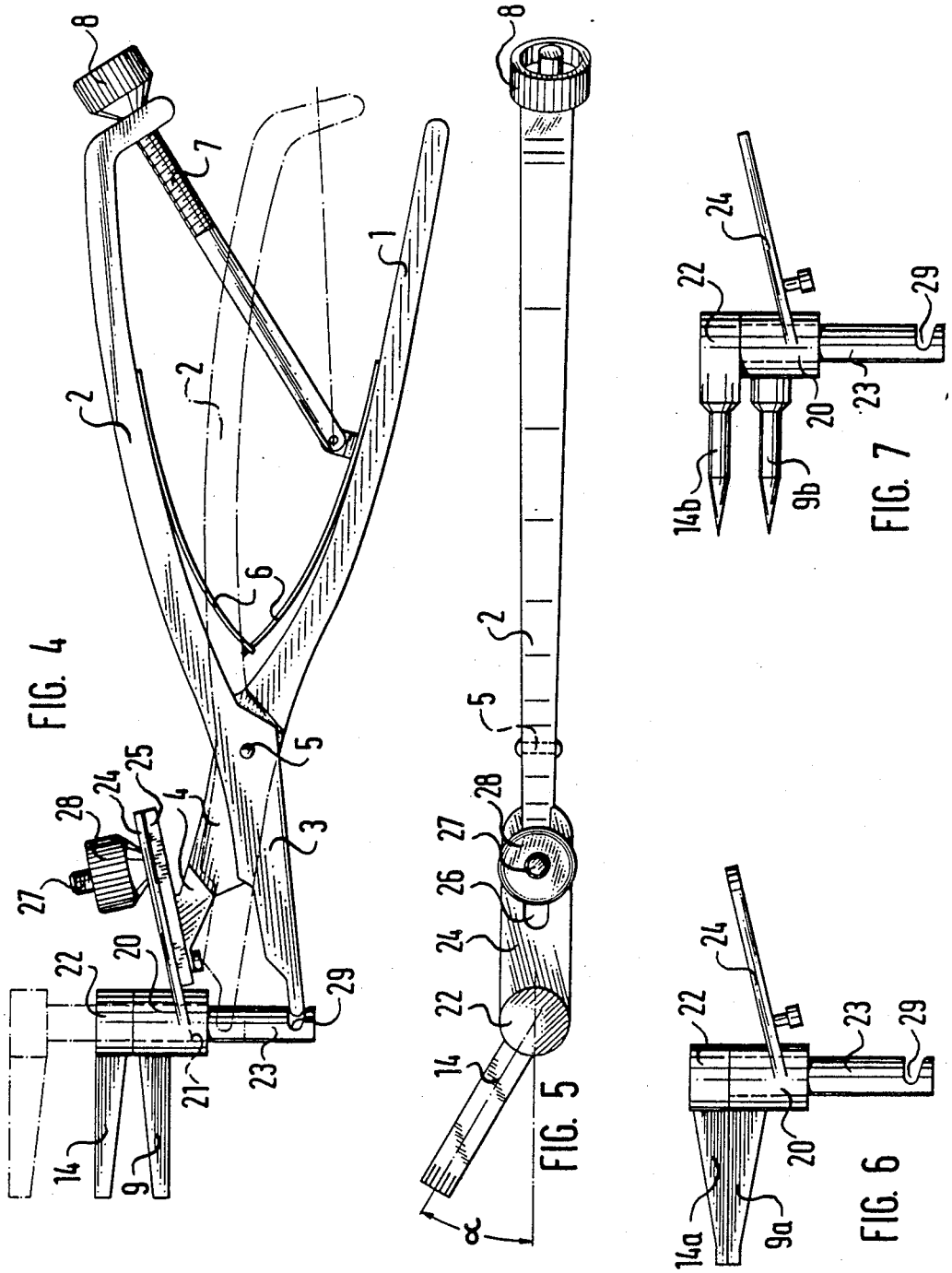

FORCEPS FOR PUSHING APART VERTEBRAE

BACKGROUND OF THE INVENTION

1. Field of the Invention

The invention relates to forceps for pushing apart adjacent vertebral column elements, comprising a pair of jaws which can be spread apart by pressing a pair of handles together.

In the event of injuries to vertebrae or spinal column discs, adjacent vertebrae are first immobilized relative to one another by metal implants, or the disc is removed wholly or partially, and the parts removed are then replaced by implants. Adjacent vertebrae are spread apart, to enable this operation to be performed.

2. Description of the Prior Art

Uncomplicated forceps have been utilized until now for spreading apart such adjacent vertebral elements, the jaws of which are opened by pushing the handles together, with an angle starting at the pivot pin of the forceps. In practice, only the extremities of the jaw branches could act, pointwise on the mutually opposed surfaces of adjacent vertebrae, so that adjacent vertebral surfaces formed a rearwardly open angle which was then filled with an implant. The resulting tilted or angled position of the vertebrae could lead to injuries to the other vertebrae and, in particular circumstances, also cause pain to the patient.

SUMMARY OF THE INVENTION

It is accordingly an object of the invention to provide forceps which will spread apart adjacent vertebrae in such a way that the mutually opposed surfaces of the adjacent vertebrae always remain parallel or substantially parallel to each other during the spreading action. According to the invention, this object is achieved in that in the case of the forceps of the type referred to above, the jaws have joined to them two parallel pins one of which may be displaced towards and away from the other, while remaining parallel thereto by means of a guiding system when the jaws are being spread apart.

In one preferred embodiment of the invention, one jaw is rigidly connected at its free end to a carrier holding one said pin, wherein the carrier is provided at right angles to the pin with a guide on which the carrier is guided, the carrier also being articulatedly coupled to the other jaw and carrying the second pin. In another embodiment the pin carrier is rigidly coupled or connected to a first jaw and provided with a perforation perpendicular to the direction of the pin as a guide for a rod which is untwistable and connected to the second jaw via a notch, and which is provided at its other end with the carrier for the second pin.

Using the forceps according to the invention, adjacent vertebrae each provided with a bore at right angles to the vertebrae column, and the two pins of the forceps are inserted into these bores, whereupon the adjacent vertebrae elements may be spread apart from each other with their mutually opposed surfaces parallel one to another, by pressing the forceps handles together and consequently causing the jaws to spread apart with concomitant movement apart of the two parallel pins, so that the damaged disc may be extracted and replaced by a metal implant, preferably a porous metal implant, which latter enters into an intimate and solid connection with the bony vertebral elements and thus also fixedly and safely interconnects the adjacent vertebral elements.

BRIEF DESCRIPTION OF THE DRAWINGS

Further objects and advantages of the invention, will become apparent from the following detailed description when read with reference to the accompanying drawings which illustrate preferred embodiments thereof.

In the drawings:

FIG. 1 shows a side view of a spreader forceps according to a first embodiment of the invention;

FIG. 2 shows a plan view of the forceps of FIG. 1,

FIG. 3 shows a vertical cross-section along the line III—III of FIGS. 1 and 2;

FIG. 4 shows a side view of a spreader forceps according to a second embodiment of the invention;

FIG. 5 shows a plan view of the forceps according to FIG. 4, and

FIGS. 6 and 7 show two interchangeable carriers with parallel pins, in side view.

DETAILED DESCRIPTION OF THE PREFERRED EMBODIMENTS

Referring to the embodiment of FIGS. 1 to 3, the forceps for the spreading apart of adjacent vertebrae comprises two handle branches 1, 2, each integrally formed with a respective jaw 3, 4 and pivotable around a spindle 5. The handles 1, 2 are held spread apart by a spring 6 whereby the jaws 3, 4 are moved towards each other. The handle 2 has a threaded shaft 7 articulated to it which traverses a bore of the other handle 1 and has a nut 8 secrewed on to its end. By turning the nut on the screw shaft, thus displacing it axially along the shaft, the relative angular position of the handles 1, 2, and hence of the jaws 3, 4, can be adjusted.

The jaw 4 is coupled to a carrier 4a which has a bore at its leading end to receive a pin 9. The carrier 4a is provided with a guide 10 perpendicular to the notionally extended axis of the pin 9, which guide has a slot 11 which is traversed by a peg 12 of a carrier 13 slidably mounted on the guide 10. The carrier 13 is provided in its leading end surface with several bores for insertion of a second pin 14 parallel to the pin 9.

The carrier 13 is provided on one side with an actuating peg 15 which passes through a slot 16 of the jaw 3. Thanks to this connection, the carrier 13 is displaced on the guide 10 when the handles 1, 2 are pushed together, whereby the parallel pins 9, 14 assume a spaced apart position in which they are inserted into previously produced parallel bores of adjacent vertebrae which they spread apart, for removal of the disc or parts thereof or for treating other injuries, when the handles 1, 2 are then pushed together by a further commensurate amount, whereupon they are kept in this position by the nut 8 screwed on the screw 7, so that the surgeon may conveniently perform the removal of the disc or disc portions and may thereupon insert rigid and preferably porous metal implants in replacement.

According to the second and very advantageous embodiment of the invention shown in FIGS. 4 to 7, the carriers bearing the pins are constructed in a simplified and exchangeable manner. In this case, the carrier 4a of FIG. 1 is replaced by a carrier 20 which is provided with an aperture 21 passing through from top to bottom perpendicular to the direction of the pin 9, a rod or bar 23 coupled to the second carrier 22 being guided by the bore so as to be axially displaceable but not rotatable about its longitudinal axis. To this end, the carrier 20 of the pin 9 is rigidly mounted on the forceps jaw 4 by an arm 24 connected to a bracket 25 provided on the jaw branch 4. To this end, the arm 24 has a slot 26 open towards one end, which upon pushing the arm 24 on to the bracket 25 together with the pins 9, 14 enflanks a screw 27 on which a nut 28 may be screwed for fixed connection of the two parts 24 and 25.

The rod 23 of the carrier 22 for the pin 14 has an elongate excision 29 into which is loosely engaged the end of the jaw 3 when the arm 24 with the carriers 20, 22 is pushed on to the bracket. By pushing the handles 1, 2 together against the spring 6, whereby the carriers 20, 22 are kept in contact, the jaws 3, 4 and thus the carriers 20, 22 bearing the pins 9, 14 are moved apart as already described with reference to FIGS. 1 to 3.

So that the surgeon's view is not obstructed by the handles 1, 2 upon spreading apart two adjacent vertebrae, it is advantageous to position the two pins in a plane which is at an angle alpha with the plane of the forceps branches 1, 2 and 3, 4 respectively, as can be seen in FIG. 5.

Thanks to the releasable connection of the pin carriers 20, 22 with the jaw branches 3, 4 of the forceps, it is possible to replace the pin carriers by carriers 20 or 22 with modified pins 9a, 9b or 14a, 14b, shown in FIGS. 6 and 7, if this is advantageous for the particular operation being carried out.

What is claimed is:

1. Forcepts for pushing apart adjacent vertebrae comprising a pair of axially parallel pins for insertion into bores in said vertebrae, a linearly sliding element guide system to enable said pins to be moved towards and away from one another while remaining mutually parallel, a pair of jaws on which said pins and said guide system are mounted, a pair of handles to actuate said jaws and effect said movement of the pins, a rod, a lateral arm, a bracket attached to one of said jaws, a first pin carrier attachable via said lateral arm to said bracket, said pin carrier provided with an aperture perpendicular to the extension of one of said pins, said aperture acting as a guide for said rod, said rod coupled at one end to the other of said jaws so as to be movable in an axial direction within said aperture, and coupled at the other end to a second pin carrier, both said pin carriers being replaceably connectable to said respective jaws.

2. Forceps as claimed in claim 1 wherein said two pins lie in a plane which is angularly offset with respect to the plane through the handles of the forceps.

* * * * *

UNITED STATES PATENT AND TRADEMARK OFFICE
CERTIFICATE OF CORRECTION

PATENT NO. : 4,898,161
DATED : February 6, 1990
INVENTOR(S) : HANS GRUNDEI

It is certified that error appears in the above-identified patent and that said Letters Patent is hereby corrected as shown below:

On the title page:

Under "Foreign Application Priority Data"

change "Dec. 12, 1986" to --Dec. 5, 1986--.

change "Mar. 3, 1987" to --Mar. 5, 1987--.

Signed and Sealed this

Thirteenth Day of August, 1991

Attest:

HARRY F. MANBECK, JR.

*Attesting Officer*     *Commissioner of Patents and Trademarks*